(12) United States Patent
Ueno et al.

(10) Patent No.: US 6,284,924 B1
(45) Date of Patent: Sep. 4, 2001

(54) COMPOUNDS

(75) Inventors: Ryuzo Ueno, Nishinomiya; Masaya Kitayama, Takarazuka; Kenji Minami, Sennan; Hiroyuki Wakamori, Hyogo-ken; Naoko Mori, Takarazuka, all of (JP)

(73) Assignee: Kabushiki Kaisha Ueno Seiyaku Oyo Kenkujo, Osaka (JP)

( * ) Notice: Subject to any disclaimer, the term of this patent is extended or adjusted under 35 U.S.C. 154(b) by 0 days.

(21) Appl. No.: 09/743,025

(22) PCT Filed: May 1, 2000

(86) PCT No.: PCT/JP00/02861

§ 371 Date: Jan. 4, 2001

§ 102(e) Date: Jan. 4, 2001

(87) PCT Pub. No.: WO00/68178

PCT Pub. Date: Nov. 16, 2000

(30) Foreign Application Priority Data

May 7, 1999 (JP) .................................................. 11-127166

(51) Int. Cl.[7] .................................................. C07C 233/00
(52) U.S. Cl. .............................. 564/153; 564/82; 564/83; 560/45; 560/56; 562/467; 548/156
(58) Field of Search ........................ 560/45, 56; 562/467; 564/153, 82, 83; 548/156

(56) References Cited

FOREIGN PATENT DOCUMENTS 60-215648 10/1985 (JP) .
63-185940 8/1988 (JP) .

*Primary Examiner*—Samuel Barts
(74) *Attorney, Agent, or Firm*—Sughrue, Mion, Zinn, Macpeak & Seas, PLLC (57) ABSTRACT

A novel compound represented by the general formula (1)

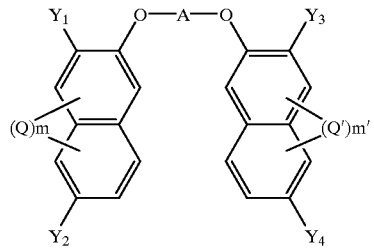

[1]

or salts thereof. The compound is useful as a structural component of polymers such as polyesters and polyamides. The compound wherein $Y_1$, $Y_2$, $Y_3$, and/or $Y_4$ are carboxy groups is especially useful as a structural component of a liquid crystal polymer with improved weld strength and anisotropy.

1 Claim, 3 Drawing Sheets

COMPOUNDS

This application is a 371 of PCT/JP00/02861 filed May 1, 2000.

TECHNICAL FIELD

The present invention relates to a novel compound useful as a structural component of polymers such as polyesters and polyamides.

BACKGROUND ART

Liquid crystal polyesters are consisted of rigid molecules which do not entangle even under the melting condition and form crystalline polydomains. The liquid crystal polyesters have low shear properties to realize a remarkably high orientation of molecular chains towards the flow. Generally, said liquid crystal polyesters are called as melted type liquid crystals or thermotropic liquid crystals. Because of their specific behaviors, said polyesters exhibit excellent melt flow properties and provide thin-wall molded articies of 0.2 through 0.5 mm in thickness Although said articles exhibit high strength and high rigidity, they have some disadvantages, including extremely large anisotropy and insufficient weld strength.

DISCLOSURE OF INVENTION

The present invention provides a novel compound which may be useful as a structural component of polyesters, polyamides or the like.

Accordingly, the present invention provides a novel compound obtainable from 2-hydroxynaphthalene-3,6-dicarboxylic acid as a starting material. This compound is important as a multifunctional monomer, which is used to prepare polyesters or polyamides with mesh or ladder structure. For example, a polyester or polyamide prepared with the compound as a structural component is expected to have significantly improved weld strength and anisotropy.

The present invention provides a compound represented by the general formula (1)

[1]

wherein $Y_1$, $Y_2$, $Y_3$, and $Y_4$ may be the same or different and represent carboxy group, an esterified carboxy group or a group of —(CONH)n—X (wherein X is an optionally branched and optionally substituted hydrocarbon group which may have unsaturated bonds, an optionally substituted aromatic group or a heterocyclic group having conjugated double bonds);
n is an integer of 1 or 2;
Q and Q' each represent an optionally branched alkyl or alkoxy group of 1–6 carbon atoms, a halogen atom, nitro group or nitroso group;
m and m' each represent an integer of 0–3; and
A represents an optionally substituted and optionally branched bivalent hydrocarbon group of 1–20 carbon atoms which may have unsaturated bonds, wherein said hydrocarbon group may have a moiety of an optionally substituted aromatic group or a heterocyclic group having conjugated double bonds;
or a salt thereof.

In the above formula, preferable esterified carboxylic groups of $Y_1$, $Y_2$, $Y_3$ and $Y_4$ include an alkoxycarbonyl group of 1–6 carbon atoms, especially, methoxy carbonyl and ethoxy carbonyl groups, phenoxy carbonyl group and phenacyl carbonyl group, wherein the aromatic moiety included in the group may have a substituent. X may include an optionally branched and optionally substituted hydrocarbon group which may have unsaturated bonds. Preferably, X may be an alkyl group of 1–20 carbon atoms, an optionally substituted aromatic group such as phenyl, naphthyl and anthraquinonyl, or an optionally substituted heterocyclic group having conjugated double bonds, such as benzimidazolonyl, carbazolyl, pyridyl, thiazolyl, benzothiazolyl, imidazolyl, indolyl, thiofuryl phenothiazinyl, acridinyl, or quinolinyl group.

Examples of substituents on those groups as above may include a halogen atom, nitro, a lower alkyl, a lower alkoxy (e.g. methoxy), cyano, phenoxy, an amidated carboxy (e.g. phenylaminocarbonyl), an esterified carboxy (e.g. methoxycarbonyl, phenoxycarbonyl), and a dialkylamino sulfonyl (e.g. diethylamino sulfonyl) groups.

When the substituent contains an aromatic ring, the compound may further have one or more substituents such as a halogen atom, a lower alkyl, a lower alkoxy, phenyl, and nitrile groups on said aromatic ring. In the present application "lower" represents a group having 1–6 carbon atoms.

In the present invention, each of the two naphthalene nuclei may have substituents of Q or Q' respectively. Each of Q and Q' may represent an optionally branched alkyl or alkoxy group of 1–6, preferably 1–4 carbon atoms, a halogen atom, nitro group and nitroso group. Each of m and m', which represents the number of the substituent, is usually 0 and may be up to 3.

In the above formula, examples of the "optionally substituted and optionally branched bivalent hydrocarbon group of 1–20 carbon atoms which may have unsaturated bonds" of A include an alkylene group (preferably a straight chain alkylene group of 1–12 carbon atoms), an alkenylene group (preferably a straight chain alkenylene group of 1–12 carbon atoms such as 2-butenylene), and an alkylene group which may have a substituent such as oxo group (preferably carbonyl, oxalyl, methylenecarbonyl and dioxo octamethylene group). Said hydrocarbon group may have a moiety of an optionally substituted aromatic group or a heterocyclic group having conjugated double bonds. Examples of the alkylene groups having therein a moiety of an aromatic group or a heterocyclic ring having conjugated double bonds include the group represented by the formulae (2) and (3). Further, a group having one or two oxo groups at the end of A, such as those represented by the formula (4), is also preferably used.

[2]

[3]

[4]

Examples of salts of the compound of the general formula (1), such as a compound wherein any one of $Y_1$, $Y_2$, $Y_3$ and $Y_4$ is carboxy group, include sodium salt and potassium salt thereof.

In one embodiment, the compound of formula (1) may be prepared according to the following scheme:

[5]    [6]    [7]

wherein $Y_1$, $Y_2$, $Y_3$, $Y_4$, Q, Q', m, m' and A are the same as above.

This reaction may usually be carried out in a conventional medium such as dimethyl formamide, under the presence of a base such as potassium carbonate. In addition, the obtained salt may be hydrolyzed, if desired, to give a carboxylic acid. In the above reaction formula, the dibromo compound (6) is used as one embodiment and other dihalogenated compound such as a dichloro compound may also be used in stead of the dibromo compound.

In another embodiment, a bisether compound of the formula (1) wherein $Y_1$, $Y_2$, $Y_3$ and $Y_4$ are different each other or wherein the molecule is asymmetric, may be prepared, for example, according to the following scheme:

[8]    [9]

[10]    [11]

[12]

wherein, $Y_1$, $Y_2$, $Y_3$, $Y_4$, Q, Q', m, m' and A are the same as above.

According to this embodiment, the mono ether compound (10) may be obtained by reacting the naphthol with a base (such as potassium carbonate), in the presence of a bromochloro compound (9), in stead of the dibromo compound (6) used in the above method, in a solvent (such as dimethyl formamide). Then the compound (11) having substituents to provide an asymmetric compound may be reacted to give the asymmetric bisether compound (12). The asymmetric compound of the present invention may be hydrolyzed to give a carboxylic acid in the same manner as of the above-described symmetric compound.

In a embodiment wherein A has one or two oxo groups on the carbon atoms at its one or both ends, the compound of the formula (1) may be obtained in the same manner as above by using a dibrominated- or dichlorinated-A compound. Alternatively, when A is a carboxylic acid or an ester thereof, the compound of formula (1) may be prepared by dehydration condensation reaction between A and 2-hydroxynaphthalene-3,6-dicarboxylic acid (8), or by ester exchanging reaction or some other well-known method.

Although an already esterified or amidated naphthol compound was then bisetherized to provide the desired compound in the above described method, the compound may be prepared by bisetherize the naphthol firstly and then esterify or amidate it. The order of the reaction is not limited.

The compound of the present invention is especially useful as a structural component polymers such as polyesters and polyamides.

The present invention is further described in reference to the following Examples. The following examples are intended to illustrate the invention and are not to be construed to limit the scope of the invention.

EXAMPLE 1

2.6 g of 2-hydroxy-3,6-dimethoxycarbonyl naphthalene was suspended in 30 g of N,N-dimethylformamide, and 0.85 g of 1,2-dibromo ethane, 2.1 g of potassium carbonate and 0.1 g of polyethylene glycol (average molecular weight of 3000) were added thereto, The mixture was reacted for 15 hours at 1 00° C. Then the reacted suspension was poured into a mixed solution consisting of 400 g of water and 100 g of methanol, the mixture was stand for about 1 hour before the precipitation was collected by means of filtration. The obtained precipitation was washed well with methanol and water, and dried to give 1.52 g of gray white powder (m.p.: 217° C.).

Figure 1:
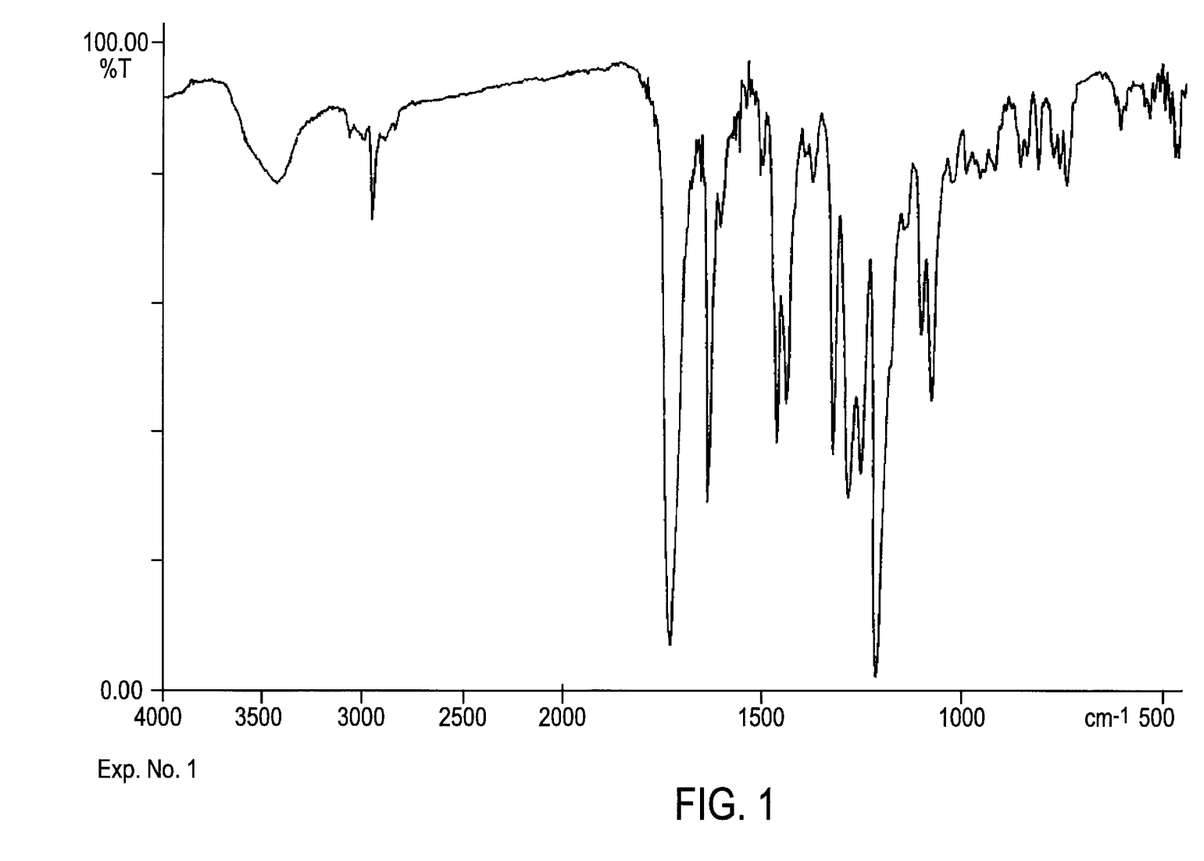
FIG. 1 is the infrared absorption spectrum (KBr) of the compound obtained in Example 1.
Figure 2:
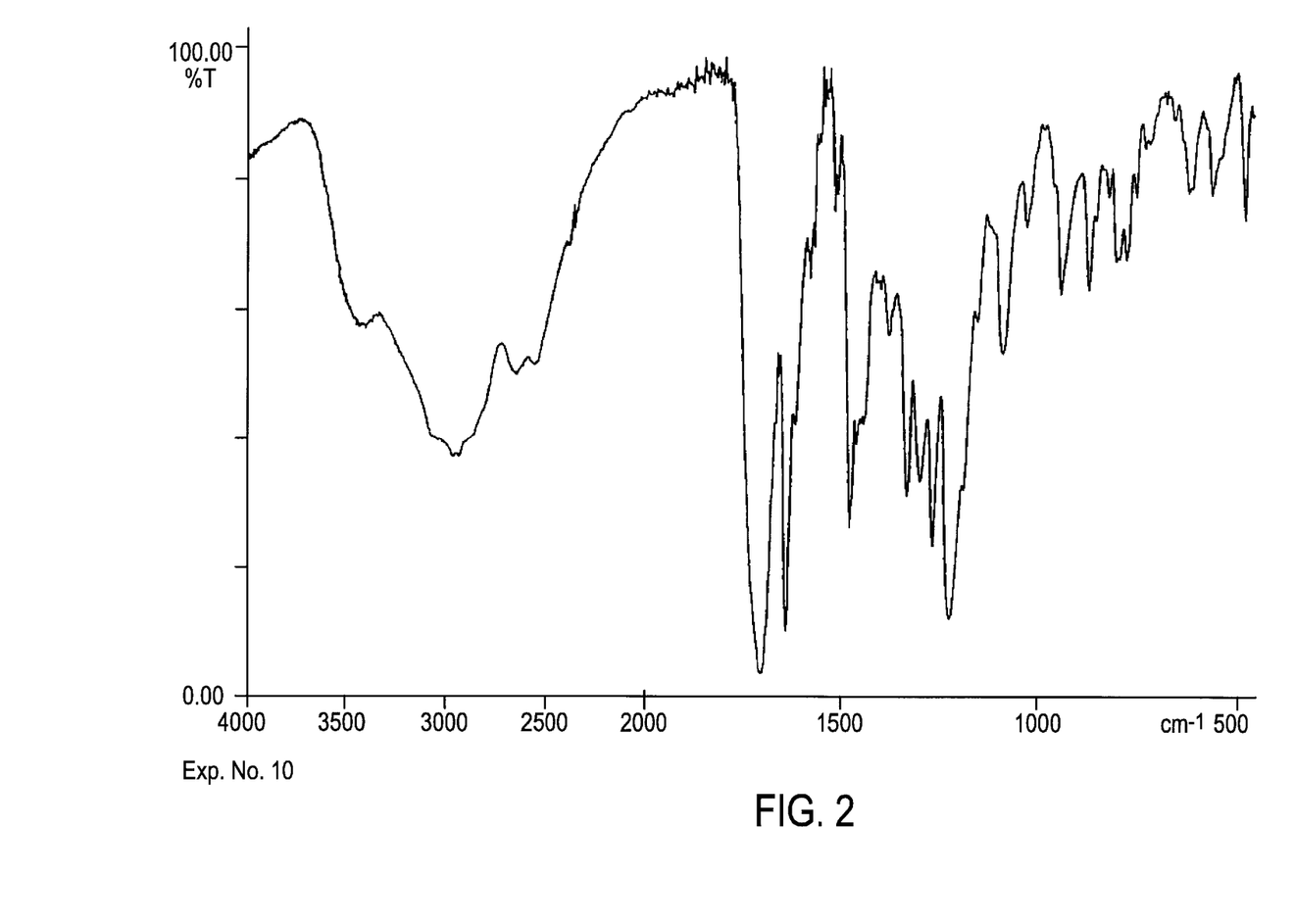
FIG. 2 is the infrared absorption spectrum (KBr) of the compound obtained in Example 10.

The infrared absorption spectrum (KBr) of the same is shown in FIG. 1.

EXAMPLES 2–9

In the same mariner as Example 1, except that the 1,2-dibromo ethane was substituted by a Br—A—Br shown in Table 1 and that 2-hydroxy-3,6-dimethoxycarbonyl naphthalene was substituted by a naphthol compound shown in Table 1, the esterified compound of the present invention was prepared. Melting points of the each of obtained compounds is shown in Table 1. (In the table 1, Me represents a methyl group, Et represents an ethyl group).

TABLE 1

| Ex. No. | Br—A—Br | naphthol of the example | structure of compound | melting point |
|---|---|---|---|---|
| 2 | Br—CH₂CH₂CH₂—Br | [HO, COOMe naphthol structure with COOMe] | [MeOOC, OCH₂CH₂CH₂O, COOMe bis-naphthalene structure] | 159° C. |
| 3 | Br—(CH₂)₄—Br | [HO, COOMe naphthol structure with COOMe] | [MeOOC, O(CH₂)₄O, COOMe bis-naphthalene structure] | 184° C. |
| 4 | Br—(CH₂)₅—Br | [HO, COOEt naphthol structure with COOEt] | [EtOOC, O(CH₂)₅O, COOEt bis-naphthalene structure] | 104° C. |
| 5 | Br—(CH₂)₆—Br | [HO, COOEt naphthol structure with COOEt] | [EtOOC, O(CH₂)₆O, COOEt bis-naphthalene structure] | 135° C. |

TABLE 1-continued

| Ex. No. | Br—A—Br | naphthol of the example | structure of compound | melting point |
|---|---|---|---|---|
| 6 | Br—(CH$_2$)$_8$—Br |  |  | 154° C. |
| 7 | Br—(CH$_2$)$_{10}$—Br |  |  | 174° C. |
| 8 | Br—(CH$_2$)$_{12}$—Br |  |  | 157° C. |
| 9 |  |  |  | 217° C. |

EXAMPLE 10

1.37 g of 2,2'-ethylenedioxy-bis(3,6-dimethoxy carbonyl naphthalene) obtained in the Example 1 was suspended in 20 g of 1,4-dioxane, and 1.0 g of sodium hydroxide and 20 g of water were added thereto. The mixture was reacted under reflux for 2 hours. The reaction mixture was cooled to the room temperature and about 1 hour before filtration, added with 40 g of water and 0.5 g of Carboraffin. The filtrate was warmed to 50–60° C. and the pH was adjusted to 2 with 10%-HCl. The mixture was stood to cool before the precipitate was collected by filtration. The precipitate was washed well with 10% aqueous methanol and dried to give 1.05 g of gray white powder (decomposition point: 318° C.).

The infrared spectrum of the composition (KBr method) is shown in Table 2.

EXAMPLES 11–18

In the same manner as Example 10, except that the 2,2-ethylenedioxy-bis(3,6-dimethoxycarbonyl naphthalene) was substituted by ester compounds indicated in Table 2, tetracarboxylic acid compounds of the present invention were prepared. The decomposition points of the obtained compounds are shown in Table 2.

TABLE 2

| Ex. No. | ester compound | structure of compound of the example | decomposition point (by TG) |
|---|---|---|---|
| 11 | compound of example 2 | HOOC-[naphthalene]-OCH₂CH₂CH₂O-[naphthalene]-COOH (with additional HOOC and COOH groups) | 315° C. |
| 12 | compound of example 3 | HOOC-[naphthalene]-O(CH₂)₄O-[naphthalene]-COOH (with additional HOOC and COOH groups) | 330° C. |
| 13 | compound of example 4 | HOOC-[naphthalene]-O(CH₂)₅O-[naphthalene]-COOH (with additional HOOC and COOH groups) | 314° C. |
| 14 | compound of example 5 | HOOC-[naphthalene]-O(CH₂)₆O-[naphthalene]-COOH (with additional HOOC and COOH groups) | 305° C. |
| 15 | compound of example 6 | HOOC-[naphthalene]-O(CH₂)₈O-[naphthalene]-COOH (with additional HOOC and COOH groups) | 292° C. |

TABLE 2-continued

| Ex. No. | ester compound | structure of compound of the example | decomposition point (by TG) |
|---|---|---|---|
| 16 | compound of example 7 |  | 273° C. |
| 17 | compound of example 8 |  | 296° C. |
| 18 | compound of example 9 |  | 280° C. |

EXAMPLES 19–29

In the same manner as Example 1, except that the 1,2-dibromo ethane was substituted by dibromo alkylenes indicated in Table 3 and 2-hydroxy-3,6-dimethoxycarbonyl naphthalene was substituted by naphthol compounds indicated in Table 3, the respective compounds of the example was synthesized. The decomposition points of thus synthesized compounds are shown in Table 3. In the table 3, Me represents methyl group, Et represents ethyl group.

TABLE 3

| Ex. | dibromo alkylene | naphthol compound | structure of compound of the example | decomposition point (by TG) |
|---|---|---|---|---|
| 19 | Br—CH₂CH₂—Br | *bis-phenyl naphthol diamide structure* | *dimer linked via OCH₂CH₂O* | 345° C. |
| 20 | Br—(CH₂)₄—Br | *bis-naphthyl naphthol diamide structure* | *dimer linked via O(CH₂)₄O* | 348° C. |

TABLE 3-continued

| Ex. | dibromo alkylene | naphthol compound | structure of compound of the example | decomposition point (by TG) |
|---|---|---|---|---|
| 21 | Br—(CH$_2$)$_8$—Br | [naphthol compound structure with CONH-phenyl-COOMe groups and OH] | [bis-naphthalene structure linked by O(CH$_2$)$_8$O with CONH-phenyl-COOMe groups] | 340° C. |
| 22 | Br—(CH$_2$)$_6$—Br | [naphthol compound structure with CONH-phenyl(MeO, SO$_2$NEt$_2$) groups and OH] | [bis-naphthalene structure linked by O(CH$_2$)$_6$O with CONH-phenyl(MeO, SO$_2$NEt$_2$) groups] | 332° C. |

TABLE 3-continued

| Ex. | dibromo alkylene | naphthol compound | structure of compound of the example | decomposition point (by TG) |
|---|---|---|---|---|
| 23 | Br—(CH$_2$)$_6$—Br |  | | 342° C. |
| 24 | Br—(CH$_2$)$_4$—Br |  | | 352° C. |

TABLE 3-continued

| Ex. | dibromo alkylene | naphthol compound | structure of compound of the example | decomposition point (by TG) |
|---|---|---|---|---|
| 25 | Br—(CH$_2$)$_4$—Br | bis-benzothiazole naphthol diamide | bis-naphthalene linked by O(CH$_2$)$_4$O with benzothiazole carboxamide groups | 347° C. |
| 26 | Br—(CH$_2$)$_5$—Br | naphthol bis(n-C$_{16}$H$_{33}$ carboxamide) | bis-naphthalene linked by O(CH$_2$)$_5$O with n-C$_{16}$H$_{33}$ carboxamide groups | 380° C. |
| 27 | Br—(CH$_2$)$_5$—Br | naphthol bis(3-nitrophenyl / phenyl carboxamide) | bis-naphthalene linked by O(CH$_2$)$_5$O with phenyl and 3-nitrophenyl carboxamide groups | 319° C. |

TABLE 3-continued

| Ex. | dibromo alkylene | naphthol compound | structure of compound of the example | decomposition point (by TG) |
|---|---|---|---|---|
| 28 | Br—CH$_2$CH$_2$—Br | | | 324° C. |
| 29 | Br—CH$_2$CH$_2$—Br | | | 268° C. |

EXAMPLE 30

In the same manner as Example 1, except that 1,2-dibromoethane was substituted by 1,4-dibromo-2-butene, 0.66 g of the compound of the above formula was obtained as pale yellow powder (melting point:205° C., decomposition point: 258° C.).

Figure 3:
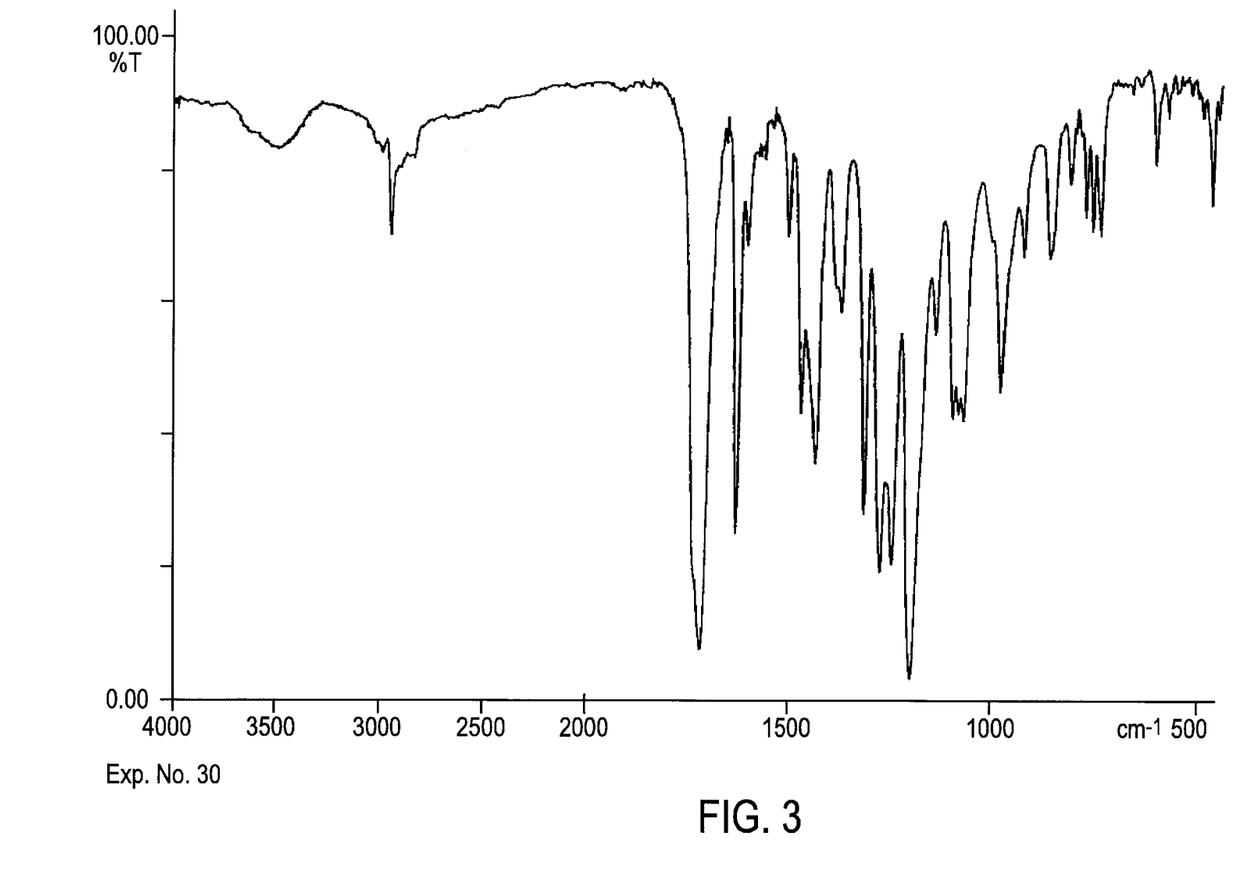
FIG. 3 is the infrared absorption spectrum (KBr) of the compound obtained in Example 30.

Infrared spectrum (KBr) of the obtained compound is shown in FIG. 3.

EXAMPLE 31

In the same manner as Example 1 except that 1,2-dibromoethane was substituted by 1.1 g of 1,4-dibromo-2,3-butanedione, the compound of the above formula was obtained as 1.8 g of pale yellow powder. (melting point: 136° C., decomposition point: 218° C.).

EXAMPLE 32

3.1 g of 2-hydroxy-3,6-dimethoxycarbonyl naphthalene was suspended in 30 g of N,N-dimethylformamide and 1.6 g of 1-bromo-3-chloropropane, 1.5 g of sodium carbonate and 0.1 g of polyethyleneglycol (average molecular weight 3000) were added thereto and reacted for 15 hours at 50° C. Then, the reaction mixture was poured into a mixed solution of 400 g of water and 100 g of methanol, about 1 hour after, the precipitates were collected by filtration. The filtrate was washed well with methanol and water and dried to give 2-(3'-chloropropyloxy)-3,6-dimethoxy carbonyl naphthalene as 2.6 g of pale yellow powder(melting point: 115° C.).

2.4 g of the obtained powder was suspended in 30 g of N,N-dimethylformamide and 3.5 g of 2-hydroxy-3-(2'-methyl phenyl)aminocarbonyl-6-n-dodecylamino carbonyl naphthalene, 1.0 g of potassium carbonate and 0.1 g of polyethylene glycol were added thereto and reacted further for 15 hours at 100° C. After the reaction was completed, the reaction mixture was poured into a mixed solution of 400 g of water and 100 g of tetrahydrofurane, and about 1 hour after, the precipitates were collected by filtration. The precipitates were washed well with water and dried to give 4.8 g of yellowish brown powder (melting point: 158° C., decomposition point: 350° C.).

EXAMPLE 33

In the same manner as Example 1, except that 1,2-dibromoethane was substituted by 0.9 g of 2,6-pyridinedicarbonyl chloride, that N,N-dimethylformamide was substituted by 50 g of sulfolane, that potassium carbonate was not added and that the reaction was carried out at 140° C., 2.5 g of the compound of the present invention having an heterocyclic ring moiety was obtained as yellowish brown powder.

INDUSTRIAL APPLICABILITY OF THE INVENTION

The compound of the present invention is useful for structural component of polymers such as polyesters and polyamides. The compound wherein $Y_1$, $Y_2$, $Y_3$ and/or $Y_4$ are carboxy groups can be preferably used as a structural component of a liquid crystal polymer because said compound is expected to significantly improve weld strength and anisotropy of the polymer.

What is claimed is:
1. A compound represented by the general formula (1)

[1]

wherein $Y_1$, $Y_2$, $Y_3$, and $Y_4$ may be the same or different and represent carboxy group, an esterified carboxy group or a group of —(CONH)n—X (wherein X is an optionally branched and optionally substituted hydrocarbon group which may have unsaturated bonds, an optionally substituted aromatic group or a heterocyclic group having conjugated double bonds);

n is an integer of 1 or 2;

Q and Q' each represent an optionally branched alkyl or alkoxy group of 1–6 carbon atoms, a halogen atom, nitro group or nitroso group;

m and m' each represent an integer of 0–3; and

A represents an optionally substituted and optionally branched bivalent hydrocarbon group of 1–20 carbon atoms which may have unsaturated bonds, wherein said hydrocarbon group may have a moiety of an optionally substituted aromatic group or a heterocyclic group having conjugated double bonds;

or a salt thereof.

* * * * *